(12) United States Patent
Srinivasan Natesan et al.

(10) Patent No.: US 10,884,718 B2
(45) Date of Patent: Jan. 5, 2021

(54) DEVICE FOR USE IN IMPROVING A USER INTERACTION WITH A USER INTERFACE APPLICATION

(71) Applicant: KONINKLIJKE PHILIPS N.V., Eindhoven (NL)

(72) Inventors: Anand Srinivasan Natesan, Chennai (IN); Rithesh Sreenivasan, Bangalore (IN); Rajendra Singh Sisodia, Bhopal (IN); Karthik Srinivasan, Bangalore (IN); Debasish Chatterjee, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/779,916

(22) PCT Filed: Nov. 30, 2016

(86) PCT No.: PCT/EP2016/079351
§ 371 (c)(1),
(2) Date: May 30, 2018

(87) PCT Pub. No.: WO2017/093362
PCT Pub. Date: Jun. 8, 2017

(65) Prior Publication Data
US 2019/0018661 A1    Jan. 17, 2019

(30) Foreign Application Priority Data

Dec. 1, 2015 (EP) ..................................... 15197290

(51) Int. Cl.
*G06F 8/38* (2018.01)
*G06N 20/00* (2019.01)
(Continued)

(52) U.S. Cl.
CPC ............... *G06F 8/38* (2013.01); *G06N 20/00* (2019.01); *G06Q 10/06* (2013.01); *G16H 10/20* (2018.01); *G16H 20/00* (2018.01)

(58) Field of Classification Search
CPC .......... G06F 8/38; G06F 3/0484; G06F 9/451; G06N 20/00; G06N 5/045; G06N 5/02;
(Continued)

(56) References Cited

U.S. PATENT DOCUMENTS

2005/0054381 A1   3/2005 Lee et al.
2005/0064916 A1   3/2005 Ozluturk et al.
(Continued)

FOREIGN PATENT DOCUMENTS

EP    1674975 A2    6/2006
WO    2006115612 A2    11/2006
(Continued)

OTHER PUBLICATIONS

Geitgey, "Machine Learning is Fun!", (May 5, 2014), <URL: https://medium.com/@ageitgey/machine-learning-is-fun-80ea3ec 3c471/>, p. 1-23 (Year: 2014).*
(Continued)

*Primary Examiner* — Ajay M Bhatia
*Assistant Examiner* — Mong-Shune Chung

(57) ABSTRACT

The present invention relates to a device (10) for use in improving a user interaction with a user interface application. It is described to provide (210) data for a user, the data comprising interaction data of the user with a plurality of interaction fields of a first version of a user interface application. The interaction data is clustered (220) into a plurality of groups. The interaction data is analysed (230) to determine the contribution a specific user interaction field of the plurality of interaction fields makes to a specific group of the plurality of groups. The specific user interaction field
(Continued)

is modified (240) on the basis of the determined contribution the specific user interaction field makes. A second version of the user interface application is displayed (250) comprising the modified specific user interaction field.

14 Claims, 4 Drawing Sheets

(51) Int. Cl.
  *G06Q 10/06* (2012.01)
  *G16H 10/20* (2018.01)
  *G16H 20/00* (2018.01)

(58) Field of Classification Search
  CPC ...... G06K 9/6223; G16H 20/00; G16H 10/20; G06Q 50/22; G06Q 10/06
  See application file for complete search history.

(56) References Cited

U.S. PATENT DOCUMENTS

| | | |
|---|---|---|
| 2011/0087501 A1 | 4/2011 | Severin |
| 2013/0298018 A1 | 11/2013 | Aqrawi et al. |
| 2014/0075336 A1* | 3/2014 | Curtis ............... G06N 20/00 715/753 |
| 2014/0372344 A1* | 12/2014 | Morris ............... G06N 5/02 706/11 |
| 2015/0026607 A1* | 1/2015 | Rapoport ............... G06F 9/451 715/762 |
| 2016/0188144 A1* | 6/2016 | Pistoia ............... H04L 67/2823 715/745 |

FOREIGN PATENT DOCUMENTS

| | | |
|---|---|---|
| WO | 2007000030 A1 | 1/2007 |
| WO | 2007078756 A2 | 7/2007 |
| WO | 2011106925 A1 | 9/2011 |
| WO | WO-2011106925 A1 * | 9/2011 ............. G06Q 30/02 |

OTHER PUBLICATIONS

Fine, N. et al., "Avoiding Average: Recording Interaction Data to Design for Specific User Groups." M. Rauterberg (Ed.): ICEC 2004, LNCS 3166, pp. 398-401, 2004, IFIP International Federation for Information Processing.

Burns, W. et al., "Mining usage data for Adaptive Personalisation of Smartphone based Help-on-Demand services" Feb. 15, 2013.

Rello, L., et al., "Guidelines and a Web Service for Making Web Text More Accessible to Dyslexics", Feb. 4, 2012.

* cited by examiner

DEVICE FOR USE IN IMPROVING A USER INTERACTION WITH A USER INTERFACE APPLICATION

CROSS-REFERENCE TO PRIOR APPLICATIONS

This application is the U.S. National Phase application under 35 U.S.C. § 371 of International Application No. PCT/EP2016/079351, filed on 30 Nov. 2016, which claims the benefit of European Patent Application No. 15197290.8, filed on 1 Dec. 2015. These applications are hereby incorporated by reference herein.

FIELD OF THE INVENTION

The present invention relates to a device for use in improving a user interaction with a user interface application, to a system for use in improving a user interaction with a user interface application, and to a method for use in improving a user interaction with a user interface application, as well as to a computer program element and a computer readable medium.

BACKGROUND OF THE INVENTION

The General background of this invention is the field of healthcare applications. Healthcare applications are used by healthcare providers to reduce readmissions and lower healthcare costs. Healthcare applications, such as an application that is accessed via a tablet or personal computer, enables the input of questions provided to the patient about their health and the input of requested measurements in order that the patient can stay connected with their care terms. The healthcare application can be used to proactively remind the patient of pre-assigned health tasks, like taking medications, and to encourage adherence to the program. However, Patients interacting with such healthcare applications are frequently elderly, and can suffer from conditions including poor vision, cognitive disabilities and frailty. These patients can have usability issues with healthcare applications which can lead to the patient dropping out of the program or to non-compliance with the program.

US2011/087501A1 describes a web-based method implemented by at least one computing device for automating a medical treatment plan. Content related to a program that is associated with a medical treatment is identified. The identified content is digitized. The digitized content is stored in a database. The identified content is provided to a patient via a user interface to assist the patient who is associated with the medical treatment.

SUMMARY OF THE INVENTION

It would be advantageous to have technique for improving a patient's compliance or adherence to a care plan.

The object of the present invention is solved with the subject matter of the independent claims, wherein further embodiments are incorporated in the dependent claims. It should be noted that the following described aspects and examples of the invention apply also for the device for use in improving a user interaction with a user interface application, system for use in improving a user interaction with a user interface application, the method for use in improving a user interaction with a user interface application, and for the computer program element and the computer readable medium.

In a first aspect, there is provided a device for use in improving a user interaction with a user interface application, comprising:
  at least one input unit;
  a processing unit;
  a display unit.

The at least one input unit is configured to provide data for a user, the data comprising interaction data of the user with a plurality of user interaction fields of a first version of a user interface application. The processing unit is configured to cluster the interaction data into a plurality of groups. The processing unit is also configured to analyse the interaction data to determine the contribution a specific user interaction field of the plurality of user interaction fields makes to a specific group of the plurality of groups. The processing unit is configured to modify the specific user interaction field on the basis of the determined contribution the specific user interaction field makes. The display unit is configured to display a second version of the user interface application comprising the modified specific user interaction field.

In other words, interaction data relating to interaction of the user with interaction fields of a user application is provided and the interaction data is clustered into groups, forming an interaction pattern. The interaction pattern (clustering) defines the level of user engagement with and adherence to the user application, and the interaction fields of the user application can be altered in order that the user is better able to engage with the user application, leading to better adherence. For example the user application can relate to a tele-health program activity and increase adherence with such a tele-health system program/activity/tasks/instructions is provided.

In this manner, interaction data relating to interaction of the user with interaction fields of a user application is provided and the interaction data is clustered into groups, forming an interaction pattern. A learning and adaptive processing is applied to in order to modify at least one of the interaction fields is modified on the basis of the interaction pattern (clustering) in order that the user can interact with the user application more optimally.

In this way, for example a user interface relating to a health plan will exhibit increased adherence by users, because they can interact with the user interface more easily, with that user interface being modified in a bespoke fashion on the basis of their needs. To put this another way, increased adherence to a care plan is provided.

Thus, the way in which a user interacts with a user application is used to assess a user's comfort level with that interaction, and the user application presented on a device the user interacts with is adaptively modified in order to improve their comfort level.

To put this another way, user interaction data of a user interacting with user interaction fields of a user application (for example for a health care application) is analysed, and interaction patterns (the clustering of data into groups) is used to infer a user's comfort level with using the user interaction fields (engagement tools) and identify intervention modes based on those patterns, enabling the user interaction fields to be modified to increase the user's level of comfort.

In this way, data generated for example as part of a care management plan can generate an optimal user interface for a specific patient based interaction data for that patient, leading to an improved bespoke care plan for that patient.

In an example, the display unit is configured to display the first version of the user interface application. An input unit of the at least one input unit is configured to capture the interaction data of the user with the plurality of interaction fields of the first version of the user interface application.

In other words, a user interacts with a user application on a device, and on the basis of the entries made and the manner in which those entries are made with respect to user interaction fields, the user interaction fields are adaptively changed in order to improve the user's interaction with the user application.

In this manner, passive monitoring of how a user interacts with a user interface application is provided and any associated challenges are identified and the user interface application is modified to mitigate those challenges.

Thus, the way in which a user interacts with a user application presented on a device is used to assess a user's comfort level with that interaction, and the user application presented on the device is adaptively modified in order to improve their comfort level.

In an example, an input unit of the at least one input unit is configured to receive the interaction data of the user with the plurality of interaction fields of the first version of the user interface application from a source external to the device.

In this manner, past interaction data of a user can be used to provide a more optimal user application interface on a device the user is now using, wherein the past interaction data could have been acquired using a different platform to the present device. For example, a user may have interacted with a user application on a PC computer with a large screen, and now the user is interacting with the user application on a smart phone. The manner in which the user interacted with the user interaction fields on the PC can be used to modify how the user interaction fields are presented on the smart phone in order to provide the user with an optimal user experience.

In an example, a decision tree model is generated on the basis of the plurality of groups. The processing unit is configured to use the decision tree model to analyse the interaction data.

In an example, the data for the user comprises interaction data of the user with the second version of the user interface application. An input unit of the at least one input unit is configured to capture the interaction data of the user with the second version of the user interface application. The processing unit is configured to analyse the interaction data to determine the contribution the modified specific user interaction field of the plurality of interaction fields makes to the specific group of the plurality of groups. The processing unit is also configured to further modify the specific user interaction field on the basis of the determined contribution the modified specific user interaction field makes. The display unit is configured to display a third version of the user interface application comprising the further modified specific user interaction field.

In this manner, interaction data relating to interaction of the user with interaction fields of a user application is provided and the interaction data is clustered into groups, forming an interaction pattern. A learning and adaptive processing is applied to in order to modify at least one of the interaction fields is modified on the basis of the interaction pattern (clustering), and this is carried out in an iterative manner tending toward an optimal solution in order that the user can interact with the user application more optimally.

In a second aspect, there is provided a system for use in improving a user interaction with a user interface application, comprising:
at least one input unit;
a processing unit.

The at least one input unit comprises a data capture unit. The data capture unit comprises a display unit. The at least one input unit is configured to provide data for a user, the data comprising interaction data of the user with a plurality of interaction fields of a first version of a user interface application. The processing unit is configured to cluster the interaction data into a plurality of groups. The processing unit is also configured to analyse the interaction data to determine the contribution a specific user interaction field of the plurality of interaction fields makes to a specific group of the plurality of groups. The processing unit is configured to modify the specific user interaction field on the basis of the determined contribution the specific user interaction field makes. The display unit is configured to display a second version of the user interface application comprising the modified specific user interaction field.

In an example, the display unit is configured to display the first version of the user interface application, and the capture unit is configured to capture the interaction data of the user with the plurality of interaction fields of the first version of the user interface application.

In an example, an input unit of the at least one input unit is a data storage device configured to provide the interaction data of the user with the plurality of interaction fields of the first version of the user interface application.

In an example, the data storage device is configured to provide data for the user that comprises health data and/or a user profile.

In this way, the ability to access the profile and use that profile for classification and improvement is provided.

This enables the contribution a user interaction field has to the clustering of data into groups (interaction pattern) to be better determined, enabling the modification to the user interaction field to be better determined.

In an example, a detailed patient (user) profile is readily available when the patient is enrolled in for example a tele health program. In this manner, the tele-health program deployment and its routine task tracking enable the progress the patient is making to be evaluated.

By providing access to a user (patient) profile, the ability to correlate interaction data of the user to the specific user profile is provided, and to correlate those interactions with the intended goal for which the user is using the user interface application, leading to improved adherence to the health program and an improved clinical outcome.

In other words, the system has 1) access to a detailed patient profile, and 2) an intended goal for which the user is using the system.

In a third aspect, there is provided a method for use in improving a user interaction with a user interface application, comprising:
a) providing data for a user, the data comprising interaction data of the user with a plurality of interaction fields of a first version of a user interface application;
b) clustering the interaction data into a plurality of groups;
c) analysing the interaction data to determine the contribution a specific user interaction field of the plurality of interaction fields makes to a specific group of the plurality of groups;
d) modifying the specific user interaction field on the basis of the determined contribution the specific user interaction field makes; and
e) displaying a second version of the user interface application comprising the modified specific user interaction field.

In an example, step c) comprises using a decision tree model generated on the basis of the plurality of groups.

In an example, classifying new interaction data into one of the plurality of groups is undertaken using the decision tree model.

In an example, the model comprises:

f) capturing interaction data of the user with the second version of the user interface application;

g) analysing the interaction data to determine the contribution the modified specific user interaction field of the plurality of interaction fields makes to the specific group of the plurality of groups;

h) further modifying the specific user interaction field on the basis of the determined contribution the modified specific user interaction field makes; and i) displaying a third version of the user interface application comprising the further modified specific user interaction field.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
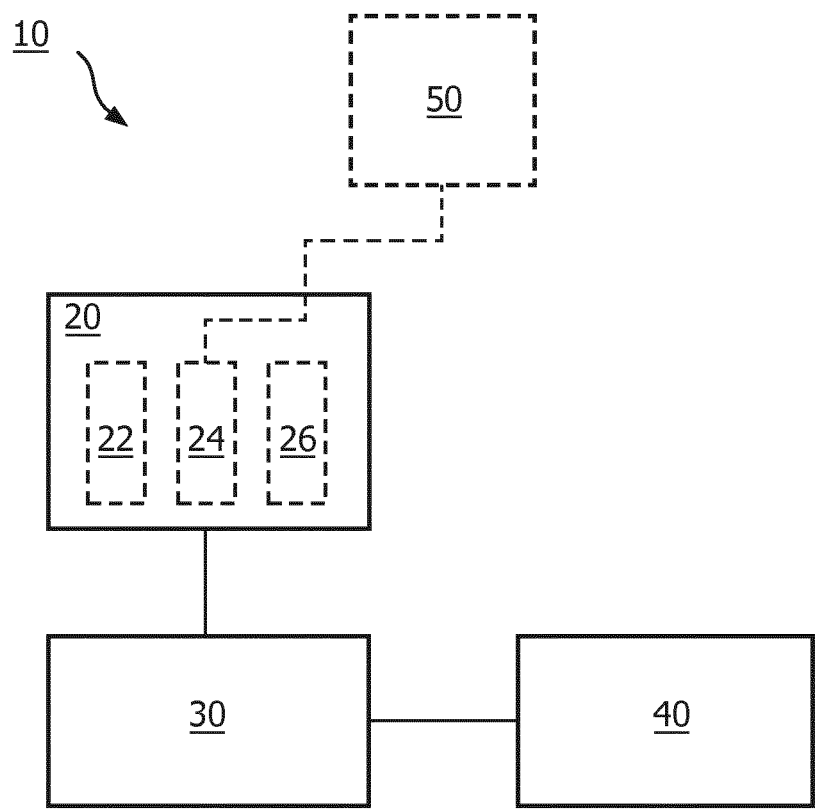
FIG. 1 shows a schematic set up of a device for use in improving a user interaction with a user interface.

FIG. 1 shows an example of a device 10 for use in improving a user interaction with a user interface application. The device 10 comprises at least one input unit 20, a processing unit 30, and a display unit 40. The at least one input unit 20 is configured to provide data for a user, the data comprising interaction data of the user with a plurality of user interaction fields of a first version of a user interface application. The processing unit 30 is configured to cluster the interaction data into a plurality of groups. The processing unit 30 is also configured to analyse the interaction data to determine the contribution a specific user interaction field of the plurality of user interaction fields makes to a specific group of the plurality of groups. The processing unit 30 is configured to modify the specific user interaction field on the basis of the determined contribution the specific user interaction field makes. The display unit 40 is configured to display a second version of the user interface application comprising the modified specific user interaction field.

Interaction data of the user with a user interaction field can relate to the user providing log-in/log-off details; the user entering data, the user navigating across and between screens, the time spent entering data. The interaction data can relate to errors made by the user or extended time spent in entering data, for example. Interaction data of the user with a user interaction field can relate to an entry being made in a wrong interaction field (for example a name being provided when a date is required to be entered), or to the skipping or missing of the entry of data (for example a forename is required to be entered followed by a surname followed by a date of birth, and the user enters their forename, does not enter their surname and moves on to entering their date of birth). This information can be analysed to automatically adjust the user interface adaptively, for example to provide text in a larger font size and/or to increase the brightness of the screen and/or increase the size of the text entering window such that it is made more clear where data is to be entered. Continued adaptive feedback leads to continual adjustment of the user interface until the clustering of interaction data indicates that the user interface is optimal for that user.

In an example, the device is a smart phone. In an example, the device is a tablet computer. In an example, the device is a laptop computer.

In an example, modifying the specific user interaction field comprises an increase in font size of text presented to the user. In an example, modifying the specific user interaction field comprises providing a voice based readout of instructions. In an example, modifying the specific user interaction field comprises providing a voice based readout of instructions in addition to a text version of those instructions presented in the earlier version of the user application. In an example, modifying the specific user interaction field comprises a decrease in the complexity of a question presented to the user. In an example, modifying the specific user interaction field comprises an increase in the window pane within which the user is required to enter data. In an example, modifying the specific user interaction field comprises omitting that user interaction field—for example if it is found that a user has particular difficult providing particular input, the requirement that the user provide that information can be skipped in order that the user is not caused distress. In this case, modifying the user interaction field can comprise the relaying of information to a health care professional in order that, for example, a person could talk to the user (such as a patient with cognitive impairment) in order to ascertain the required information. In this manner, if required shorter surveys and/or with less complex questions can be provided.

In an example, the processing unit utilizes a k-means algorithm to cluster the interaction data. In an example, the processing unit utilizes a hierarchical algorithm to cluster the interaction data.

In an example, a machine learning algorithm is used to analyse the interaction data. In an example, the machine learning algorithm comprises a SVM network. In an example, the machine learning algorithm comprises a Neural network.

According to an example, the display unit 40 is configured to display the first version of the user interface application. An input unit 22 of the at least one input unit 20 is configured to capture the interaction data of the user with the plurality of interaction fields of the first version of the user interface application.

According to an example, an input unit 24 of the at least one input unit 20 is configured to receive the interaction data of the user with the plurality of interaction fields of the first version of the user interface application from a source 50 external to the device.

According to an example, a decision tree model is generated on the basis of the plurality of groups, and the processing unit 30 is configured to use the decision tree model to analyse the interaction data.

In an example, the decision tree model is configured to classify new interaction data into one of the plurality of groups. In this manner, an optimal solution can be continually improved in an adaptive way.

In an example, the decision tree model is configured to classify the user into a particular group. For example, a group could relate to a user having a visual impairment or having a cognitive impairment or to a user being frail, or to a user having two or more of these conditions, and a grouping can relate to "normal" interactions. Then, as the user interaction fields are modified based on the user interactions, in order to improve the user interaction, the user interactions can move into the "normal" grouping and for example at some point the interactions for that user are considered to be normal and the user application for that user is optimal. However, this user application leading to a normal grouping could be quite different to that for a different user, depending upon their user interactions.

In an example, a machine learning algorithm is used to generate the decision tree model. In an example, a decision tree based machine learning algorithm is used to generate the decision tree model. In an example, an ID3 algorithm is used to generate the decision tree model. In an example, a C4.5 algorithm is used to generate the decision tree model.

In an example, use of the decision tree model to analyse the interaction data comprises performance of deep dive analysis.

According to an example, the data for the user comprises interaction data of the user with the second version of the user interface application. An input unit 26 of the at least one input unit is configured to capture the interaction data of the user with the second version of the user interface application. The processing unit 30 is configured to analyse the interaction data to determine the contribution the modified specific user interaction field of the plurality of interaction fields makes to the specific group of the plurality of groups. The processing unit 30 is also configured to further modify the specific user interaction field on the basis of the determined contribution the modified specific user interaction field makes. The display unit 40 is configured to display a third version of the user interface application comprising the further modified specific user interaction field.

In an example, the data for the user comprises health data and/or a user profile. In this manner, recommendations can be arrived at more effectively for how the user interface application can be more effectively presented for a user. In other words, the clustering of interaction data into groups (interaction pattern determination) can be fined tuned using domain knowledge (e.g. information on the user). For example, in a health care situation where a user application relates to a heart condition, prior acquire knowledge relating to the user (e.g. patient) can be used. For example, the health data could indicate that the user has a visual impairment, or has cognitive disabilities, and this information is used by the processing unit in clustering the interaction data into the plurality of groups. Thus, the contribution a specific user interaction field makes to a grouping of data can be better determined, thereby enabling a user interaction field to be modified in an optimal manner. In an example, the health data and/or user profile, is used in labelling the user (classifying the user into a group).

In an example, health data comprises data acquired by medical devices, such as a weight scale, oximeter, blood pressure meter and medicine dispenser, and enables a deeper insight into patient health.

In an example, the input unit 22 configured to capture the interaction data of the user with the plurality of interaction fields of the first version of the user interface application is same as the input unit 26 configured to capture the interaction data of the user with the second version of the user interface application.

Figure 2:
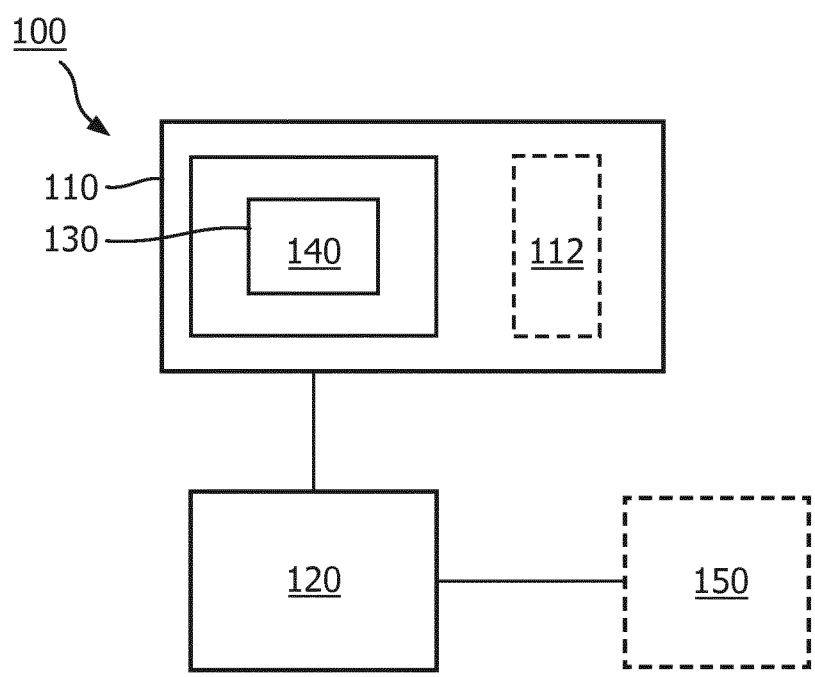
FIG. 2 shows a schematic set up of a system for use in improving a user interaction with a user interface.

FIG. 2 shows an example of a system 100 for use in improving a user interaction with a user interface application. The system 100 comprises at least one input unit 110, and a processing unit 120. The at least one input unit 110 comprises a data capture unit 130. The data capture unit 130 comprises a display unit 140. The at least one input unit 110 is configured to provide data for a user, the data comprising interaction data of the user with a plurality of interaction fields of a first version of a user interface application. The processing unit 120 is configured to cluster the interaction data into a plurality of groups. The processing unit 120 is also configured to analyse the interaction data to determine the contribution a specific user interaction field of the plurality of interaction fields makes to a specific group of the plurality of groups. The processing unit 120 is configured to modify the specific user interaction field on the basis of the determined contribution the specific user interaction field makes. The display unit 140 is configured to display a second version of the user interface application comprising the modified specific user interaction field.

According to an example, the display unit 140 is configured to display the first version of the user interface application, and the capture unit 130 is configured to capture the interaction data of the user with the plurality of interaction fields of the first version of the user interface application.

According to an example, the display unit 140 is configured to display the first version of the user interface application, and the capture unit 130 is configured to capture the interaction data of the user with the plurality of interaction fields of the first version of the user interface application.

In an example, a decision tree model is generated on the basis of the plurality of groups, and the processing unit is configured to use the decision tree model to analyse the interaction data.

In an example, the decision tree model is configured to classify new interaction data into one of the plurality of groups.

In an example, the decision tree model is configured to classify the user into a particular group.

In an example, use of the decision tree model to analyse the interaction data comprises performance of deep dive analysis.

In an example, the data for the user comprises interaction data of the user with the second version of the user interface application. An input unit of the at least one input unit is configured to capture the interaction data of the user with the second version of the user interface application. The processing unit is configured to analyse the interaction data to determine the contribution the modified specific user interaction field of the plurality of interaction fields makes to the specific group of the plurality of groups. The processing unit is also configured to further modify the specific user interaction field on the basis of the determined contribution the modified specific user interaction field makes. The display unit is configured to display a third version of the user interface application comprising the further modified specific user interaction field.

According to an example, the data storage device 112 is configured to provide data for the user that comprises health data and/or a user profile.

In an example, the system comprises as output unit 150 configured to output data relating to the user. In an example, the output data comprises recommendations coming out of the analysis of the interaction data. In this manner, additional intelligence is provided relating to when a specific type of education needs to be presented to the user.

Figure 3:
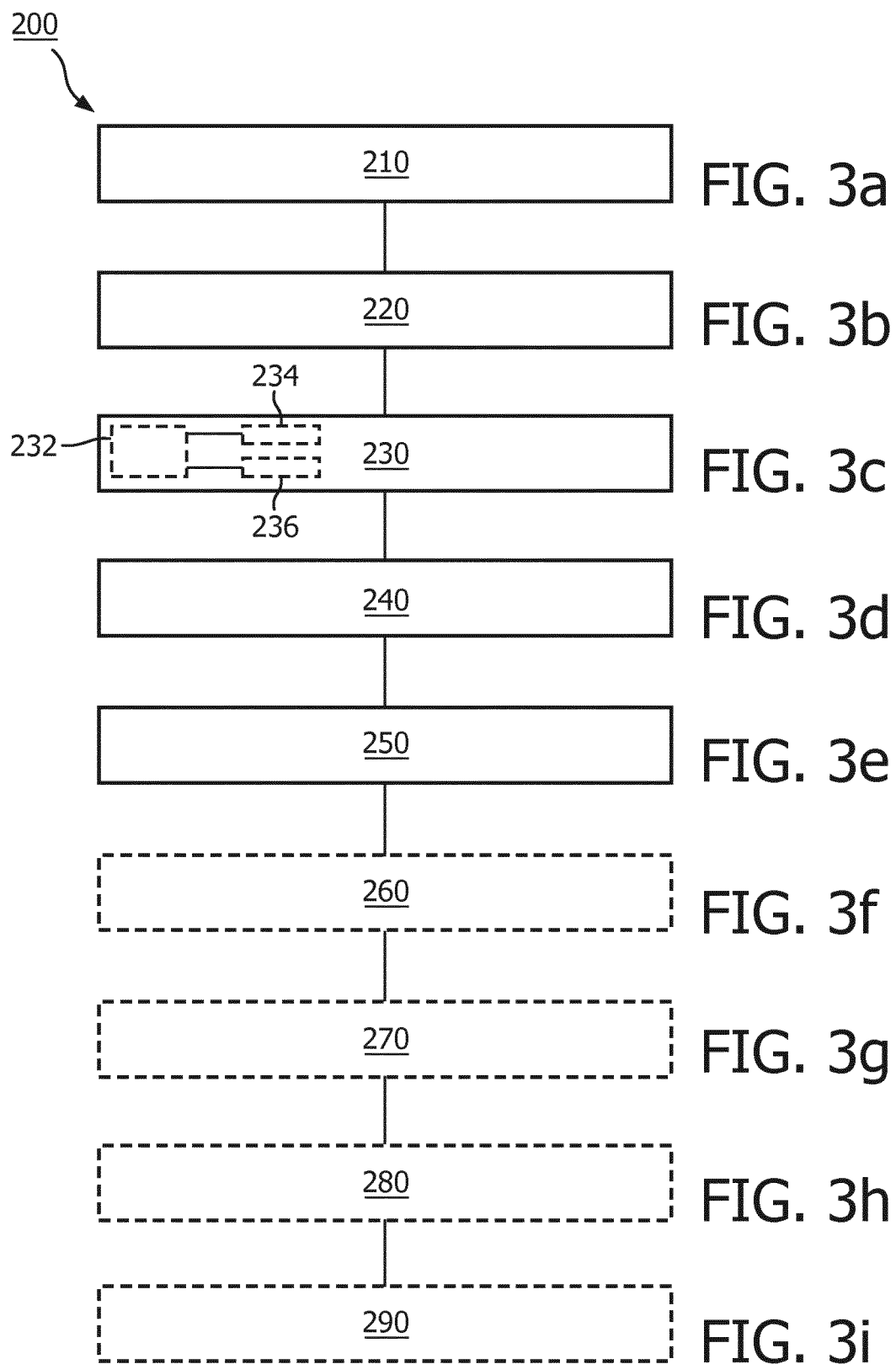
FIG. 3 shows a method for improving a user interaction with a user interface.

FIG. 3 shows a method 200 for use in improving a user interaction with a user interface application in its basic steps. The method 200, comprises:

In a providing step 210, also referred to as step a), data for a user is provided, the data comprising interaction data of the user with a plurality of interaction fields of a first version of a user interface application;

In a clustering step 220, also referred to as step b), the interaction data is clustered into a plurality of groups;

In an analyzing step 230, also referred to as step c), the interaction data is analyzed to determine the contribution a specific user interaction field of the plurality of interaction fields makes to a specific group of the plurality of groups;

In a modifying step 240, also referred to as step d), the specific user interaction field is modified on the basis of the determined contribution the specific user interaction field makes; and In a displaying step 250, also referred to as step e), a second version of the user interface application is displayed comprising the modified specific user interaction field.

According to an example, step c) comprises using 232 a decision tree model generated on the basis of the plurality of groups.

According to an example, classifying 234 new interaction data into one of the plurality of groups is undertaken using the decision tree model.

In an example, classifying 236 the user into a particular group is undertaken using the decision tree model.

In an example, analysing the interaction data comprises performing a deep dive analysis.

According to an example, the method comprises:

In a capturing step 260, also referred to as step f), interaction data of the user is captured with the second version of the user interface application;

In an analysing step 270, also referred to as step g), the interaction data is analysed to determine the contribution the modified specific user interaction field of the plurality of interaction fields makes to the specific group of the plurality of groups;

In a further modifying step 280, also referred to as step h), the specific user interaction field is further modified on the basis of the determined contribution the modified specific user interaction field makes; and In a displaying step 290, also referred to as step i), a third version of the user interface application is displayed comprising the further modified specific user interaction field.

The device, system, and method for use in improving the user interaction with user interface application is now described in more detail with reference to FIGS. 4 and 5 and Table 1.

The present healthcare user interface application is used by a wide variety of patients. Frequently, it is used by older patients. These patients can have conditions, such as:

poor (or low) vision;
cognitive disabilities; and
frailty.

These patients can have usability issues:

for people with reading/cognitive challenges, they can find it difficult to complete complex surveys;

for people having to provide feedback relating to measurement tasks, incorrect feedback can be provided. This can be termed "misconfiguration scenarios related to measurement tasks", where for example the misconfiguring of units of measurements or the using of different of values for different measuring devices can lead to confusion for patients as they may have to convert values in order to enter data, and then they can enter such data incorrectly;

for people with poor vision, they can have difficulty in using the applications and delay in completing tasks, which can be exacerbated by the misconfigurations of the tablet or smartphone on which the user application is presented (e.g. frequent change of brightness level (dimming to save battery).

By detecting these usability issues, feedback can be provided in the form of recommendations. The user interface can then be improved (e.g. rectified) leading to better patient adherence and better clinical outcomes. For a patient with weak (or poor or low) eyesight, the recommendation can be to increase the font size in the application. For a person with cognitive disability a complex survey can be redesigned as a simple survey.

In the case of a healthcare application, some interaction modes are as follows:

1) Patients are asked to perform certain activities as per a clinical plan;

2) Applications in the remote device (tablet or smartphone) are provided to the user, and these are capable of supporting those activities. These activities may be stand-alone activities performed by single application or with multiple applications.

The user interacts with these applications, to perform the above activities, and in doing so interaction patterns are generated within or between applications. In other words, the user will input data incorrectly in certain ways and in relation to some tasks more than others, and will take longer to complete certain tasks than others. Thus the interaction of the user with user interaction fields leads to the generation of user interaction data, and this interaction data can be used to generate interaction patterns. The manner in which the user interacts with user interaction fields and the impact this has on the interaction patterns can be analyzed in order to improve the user interaction fields within the user interface, such that the user can interact more effectively with the user application.

Overview

A usability survey task and application logging framework, for logging interactions of the patient with the personalized application, are provided. The logged interactions are then automatically segregated into groups. Machine learning is applied to the subset of the grouped data. The learned model is applied on the whole interaction data. Deep dive analysis of this data is used for generating recommendations for improving the usability issues of the personalized application for better a clinical outcome for the patient. Interaction pattern(s) are correlated with the progression of clinical conditions and patient conditions (ability to comprehend, engagement and also ability to perform tasks and speed of completing tasks). The personalized application is then modified (designed/deployed) in order to be specific to a patient condition(s) and the tasks presented to the user are modified in order that the patient can interact more optimally with the application, leading to reduced patient frustration, and improved adherence and/or compliance with the care plan.

Main Elements

The main elements of are:
1. Determining usability issues of the patient using a predefined survey task.
2. A logging framework on the patient facing application to capture the raw interaction data and convert it into processed data.
3. Clustering and labelling users into similar interaction groups based on the processed data
4. Learning interaction patterns based on a machine learning algorithm, by building a model from the grouped data.
5. A recommendation framework to deep dive analysis and provide recommendations using the machine learned interaction analysis model.
   a. The recommendations can be in the form of automatic adaption of the user interface, in order that the user interface application become bespoke for that patient, and enables them to interact optimally with the application, and/or
   b. The providing of recommendations to an application developer, who then implements the optimal application design for better patient interaction.

Figure 4:
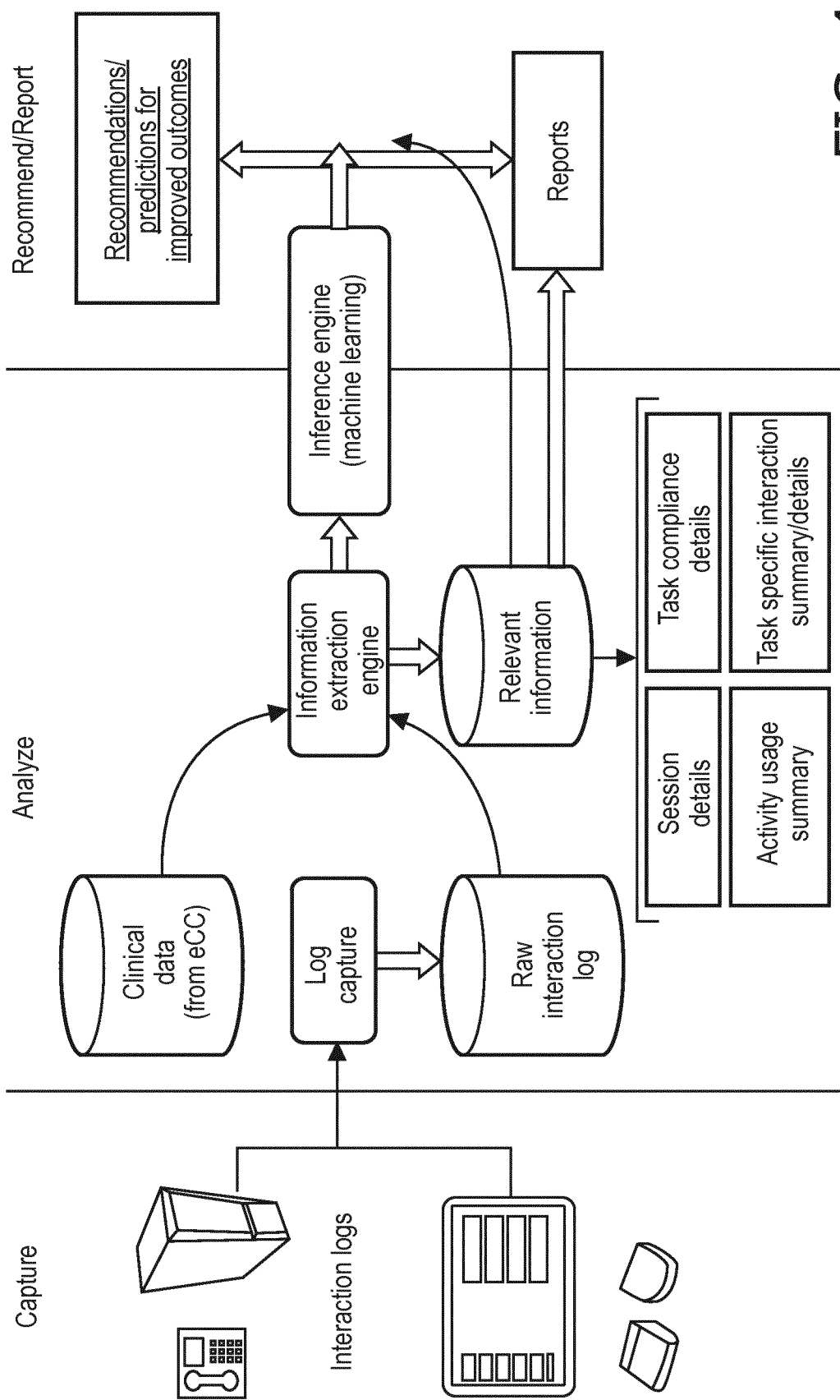
FIG. 4 shows a schematic set up of a system for use in improving a user interaction with a user interface.

FIG. 4 shows a detailed system architecture for use in improving a user interaction with a user interface application. The system consists of the three layers: (1) data capture layer (2); data analyze layer (3); and recommendation/reporting layer.

Data Capture Layer:

The patient facing application provides the patient with user interfaces to enter measurement data, answer surveys, view video content and look at measurement trends. It also includes the patient facing application that is connected to medical devices to upload clinical measurements or the patient may manually enter the clinical readings. The interactions of the patients with the application are captured in the form of interaction logs.

Data Analyze Layer

In this layer the raw interaction logs are processed and converted into relevant information by the information extraction engine. The inference engine uses a machine learning technique (clustering/labelling/classification) to analyse this information.

Recommendations/Reporting Layer

In this layer, based on the results of the inference engine, the recommendations/reports are generated.

Figure 5:
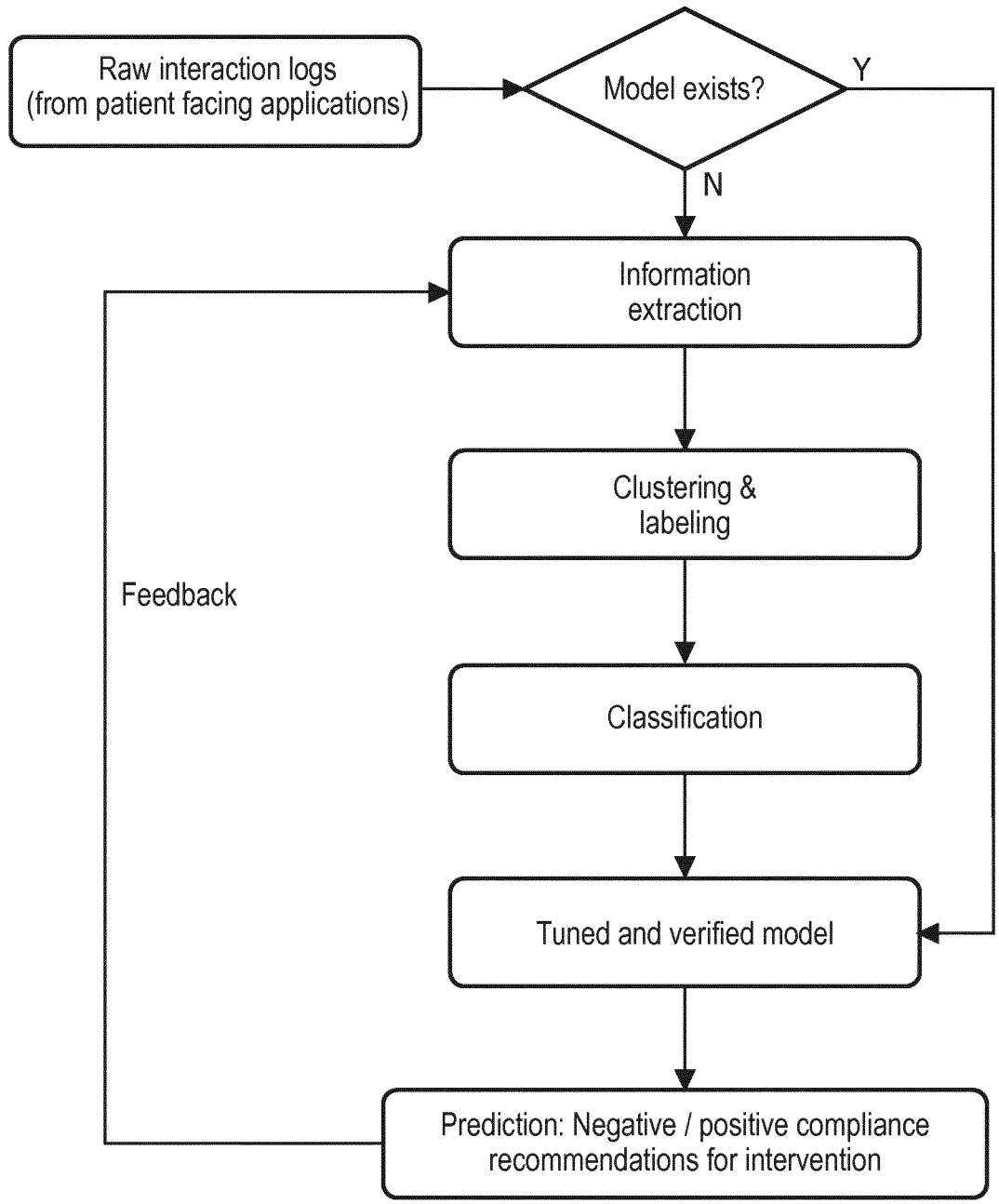
FIG. 5 shows a workflow for operation of a machine learning algorithm for use in improving a user interaction with a user interface.

FIG. 5 shows the creation and usage of the prediction model from the raw interaction logs using unsupervised and supervised techniques. Points 1-5 below then provide further detail on the device, system and method.

1) A Survey Task Designed to be Sent to the Patient to Identify Usability Issues The survey task can have the following sub tasks:
a) The survey task includes a set of sub task(s) to identify (quantify) the vision or visual capability of the patient. For instance the patient is presented with flash cards of different font sizes to determine which font size he/she is more comfortable with.
b) The survey tasks involve a set of sub task(s) to identify (quantify) cognitive ability of the patient. For instance the patient is presented with a memory based games or simple correlation tasks.
c) The survey task includes a set of sub task(s) for identifying frailty. For instance accelerometer based activity can be given to the patient to identify his locomotive skills.

An Exemplar Design of the Survey Task is Described Below:

The survey task is presented as a series of different levels of complexity or difficulty. The user has to complete the levels. The comprehension ability of the user can be analysed by looking at the level he has reached. For instance, data can be presented as a pie chart in one level, a 3D graph chart in the next level, and a fish bone representation in the last level. The users are asked questions to understand the comprehension capability for each graph based on which different difficulty level is assessed.

Based on how the person performs in achieving the levels, information relating to the comprehension, attention span, engagement etc is provided. Based on this input (interaction pattern) the application or next tasks are designed such that it fits the user profile, along with their usability features.

2) A Logging Framework/Information Extraction Framework on a Patient Facing Application to Capture the Raw Interaction Data and Convert it into Processed Data.

The logging framework captures patient interaction with respect to the previous survey task as well as any other tasks related to system level changes. For instance brightness levels, Wi-Fi signal, battery levels etc. are all captures as well. The above framework can also be used to capture interactions between applications.

3) Clustering & Labelling Algorithm to Group the Interaction Logs

An unsupervised approach using k-means a clustering algorithm (hierarchical clustering could be used instead of K-means clustering) is applied to the data generated in the interaction logging framework. The clusters are further fine-tuned using domain knowledge. For example, if the care plan is for heart failure patients and a survey before the care plan start has identified other co-morbid conditions and cognitive disabilities, this information is fed into the clustering algorithm as domain knowledge. Along with the above data, the patient's response to the initial survey task is fed to the clustering algorithm which is used for labelling the users. A sample set of groups into which the processed interaction data can be grouped into are: Normal, Patients with UX issues, Patients with low vision, Frail patients with low vision, Patients with dementia and Patients with compliance issues. Other groupings are possible.

4) Machine Learning Algorithm for Modelling and Classification of Clustered and Labelled Data.

A machine learning algorithm like SVM/Neural network is applied to model the clustered and labelled interaction data. The output of the learning algorithm is a classifier to make predictions based on the interaction data. A sample set of groups into which the patient may get classified as prediction are: Normal, Patients with UX issues, Patients with low vision, Frail patients with low vision, Patients with dementia and Patients with compliance issues.

5) A Recommendation Framework to Deep Dive Analysis and Provide Recommendations Using the Machine Learned Model.

The recommendation framework takes the output from the machine learning classifier and applies it on the interaction data one instance at a time. It then performs analytics based on the prediction to identify the most significant contributing factors. Based on the contributing factors the recommendations are chosen from a recommendation library. The recommendations are then applied on the patient application, either automatically or via an application developer modifying the application. For instance a recommendation for a patient predicted with usability issues concerned with low vision may be an increased brightness, increased font size and simple icons.

The inference engine provides the following:
1. The recommended application changes are presented again as a task to the patient app.
2. Based on tasks which are pushed to the users interaction, items within apps which are responsible for those tasks (buttons, etc.) are highlighted and the rest are disabled.
3. Based on the response to the task, the application configuration is changed. During the response to the task the patient can approve the changes or neglect the changes. For a patient with cognitive disabilities or dementia, recommendation are provided to the clinician so that he can design simple surveys, or the simple surveys are automatically implemented. For instance a complicated survey with lot of questions, which refers to responses from previous questions, can be reduced to a simple surveys with fewer references to responses of previous questions.
4. Once the patient/clinical users accepts the recommendations, the patient is further monitored for improved adherence to the changes as well as to the care plan. The assumption in the design of a whole care plan is that if a patient adheres to the care plan, clinical outcomes are positive. Therefore, the present device, method and system provides for an improved clinical outcome.
5. The clinician or app developers can be presented with a heat map of the patient interactions with the application to determine the optimal application design for best interaction, in addition to the user interface being automatically adapted.

Data Capture and Analysis—Further Details
Data Capture
1. Data (Interaction Events) is Captured (as Shown in Table 1.)

The data as shown in Table 1 is captured using the interactions logging framework which is built into the healthcare application using application logic as well as using system events provided by an operating system (for example android). If the healthcare application were to be implemented on any other platform the same can be provided by the other platform. The data is captured as the subject/patient interacts/makes use of the healthcare application. Along with this data capture, information like care plan, co-morbid conditions, physical and cognition levels are captured from the patient profile held on a data storage device (shown as eCC in FIG. 4).

Data Analysis
2. Interaction Pattern are Formed (Continuous Wrong Entry in Text Fields, Skipping of Surveys) Based on Either Sequence of Events or Results of Events—(Formation of the Interaction Pattern is Termed Clustering)

The data generated in the previous step is provided in the form of a row vector, with values for each of the interaction fields. Such rows form a table of data on which the k-means clustering algorithm (further details provided below) is applied. The algorithm generates the initial clustering, which is then fine-tuned using the domain knowledge. For instance, for a patient whose care plan is for heart failure, a survey before the care plan start has also identified other co-morbid conditions and cognitive disabilities. This information is fed to the clustering algorithm, which is used for labeling the users. The patients are classified into set of groups based on the processed interaction data as: Normal; Patients with UX issues; Patients with low vision; Frail patients with low vision; Patients with dementia; and Patients with compliance issues. The grouping is not limited to the above and can change dynamically based on new interaction data. The clustering algorithm is also not limited to k-means. Other clustering algorithms present in literature can be used depending upon the accuracy of the clustering algorithm.

Aggregation of Analysed Data (Model Generation)
3. An Interaction Model is Created, Combining Patient Profile and Interaction Pattern (Combining Clustering/Machine Learning)

The groups of data obtained in the previous step are known as the training data. Decision Tree based machine learning algorithm (further details provided below) is used to generate a decision tree model on the training data. This model is used for classifying new interaction data into one of the groups. The decision tree model also identifies which field contributes more to the grouping. For instance, for the patients in the group "Frail patients with low vision" it identifies that these patients have the highest erroneous entries while entering measurements in the measurement entry screen. In another instance where the patient is in the group "Patient with dementia" the algorithm identifies that the patient has not completed the survey tasks on many instances.

Other machine learning algorithms present in literature can also be used to generate different classification models.
4. Generation of a Preferred Interaction Model is Generated (More Detail on an Example of Step 3)

The decision tree model generated is run on the processed patient interaction data captured in step 1. The model classifies the patient into a particular group. Further deep dive analysis (further details provided below) is performed by the algorithm to identify the contribution of each interaction field to the grouping. This results in identifying the contributing factors, like cognitive ability, physical condition of patient, screens or activities, tasks and other user interaction issues where the patient is having trouble interacting with the application.

For instance, for the patients in the group "Frail patients with low vision" it identifies that these patients have the highest erroneous entries while entering measurements in the measurement entry screen. The intervention as sent back to the application as an increase in screen font size as well as a voice based readout of the instructions and voice based entry for instructions.

In another instance where the patient is a dementia patient the algorithm identifies that the patient has not complete the survey tasks on many instances. The intervention is sent back to eCP application as shorter surveys with less complex questions.

Use of the Model—the Interventions and Associated Application Changes Constitute the Preferred Interaction Model.
5. This Preferred Interaction Model (from Step 3 or 4) is Translated into Series of Preferred Interaction Pattern and the Interaction Patterns are Deployed As in the previous example, the preferred interaction model for a frail and low vision patient would result in an increase in screen font size as well as a voice based readout of the instructions and voice based entry for instructions. This change is deployed on the healthcare application.

As in the previous example of dementia patients, shorter surveys with less complex questions are deployed on the application.

6. Events are Captured.

The patient interacts with the newly deployed system (healthcare application) and the interactions are further captured and refined using steps 1 to 5 until the required results are achieved.

When the interactions have improved, the "frail patients with low vision" would get classified as "normal patients" in the classification—this is because they are then interacting as anticipated for the updated healthcare application. This means that the patient compliance and user interaction issues have been resolved.

The following provides further details on parts of the modeling utilized.

K-Means Clustering

The Algorithm

K-means (MacQueen, 1967) is one of the simplest unsupervised learning algorithms that solves a clustering problem. The procedure follows a simple and easy way to classify a given data set through a certain number of clusters (assume k clusters) fixed a priori. The main idea is to define k centroids, one for each cluster. These centroids should be placed in a cunning way because different locations causes different results. So, the best choice is to place them as far away from each other as possible. The next step is to take each point belonging to a given data set and associate it to the nearest centroid. When no point is pending, the first step is completed and an early groupage is done. At this point we need "k" new centroids are re-calculated as barycenters of the clusters resulting from the previous step. After these k new centroids have been determined, a new binding has to be done between the same data set points and the nearest new centroid. A loop has been generated. As a result of this loop the k centroids change their location step by step until no more changes are done. In other words, finally the centroids do not move any more.

Finally, this algorithm aims at minimizing an objective function, in this case a squared error function. The objective function $$J = \sum_{j=1}^{k} \sum_{i=1}^{n} \|x_i^{(j)} - c_j\|^2, \text{ where } \|x_i^{(j)} - c_j\|^2$$

is a chosen distance measure between a data point $x_i^{(j)}$ and the cluster centre $c_j$, is an indicator of the distance of the n data points from their respective cluster centres.

The algorithm is composed of the following steps:
1. Place K points into the space represented by the objects that are being clustered. These points represent initial group centroids.
2. Assign each object to the group that has the closest centroid.
3. When all objects have been assigned, recalculate the positions of the K centroids.
4. Repeat Steps 2 and 3 until the centroids no longer move. This produces a separation of the objects into groups from which the metric to be minimized can be calculated.

Although it can be proved that the procedure will always terminate, the k-means algorithm does not necessarily find the most optimal configuration, corresponding to the global objective function minimum. The algorithm is also significantly sensitive to the initial randomly selected cluster centres. The k-means algorithm can be run multiple times to reduce this effect.

K-means is a simple algorithm that has been adapted to many problem domains. It is also a good candidate for extension to work with fuzzy feature vectors.

Decision Tree

C4.5 builds decision trees from a set of training data in the same way as ID3, using the concept of information entropy. The training data is a set $S=s_1, s_2, \ldots$ of already classified samples. Each sample $s_i$ consists of a p-dimensional vector $(x_{1,i}, x_{2,i}, \ldots, x_{p,i})$, where the $x_j$ represent attribute values or features of the sample, as well as the class in which $s_i$ falls.

At each node of the tree, C4.5 chooses the attribute of the data that most effectively splits its set of samples into subsets enriched in one class or the other. The splitting criterion is the normalized information gain (difference in entropy). The attribute with the highest normalized information gain is chosen to make the decision. The C4.5 algorithm then recurs on the smaller sublists.

This algorithm has a few base cases.

All the samples in the list belong to the same class. When this happens, it simply creates a leaf node for the decision tree saying to choose that class.

None of the features provide any information gain. In this case, C4.5 creates a decision node higher up the tree using the expected value of the class.

Instance of previously-unseen class encountered. Again, C4.5 creates a decision node higher up the tree using the expected value.

Deep Dive Analysis

Deep dive is an data analysis system that enables data extraction, integration and prediction. In provides the ability to determine the parts of an application that can be adapted to improve the quality of the application. Deep Dive uses machine learning to mitigate noise and imprecision, providing the ability to solve statistical inference problems. Deep Dive was developed by Stanford University, and the skilled person can refer to standard literature for further details.

Below are Further Details on how the Interaction Model is Developed and Used for Improved Interactions.

In summary, it is a 6 steps process

Example 1

1. Interaction events capture (raw data capture): e.g wrong entry in a particular field.
2. Interaction patterns are generated (classification of way patient is interacting for specific tasks/service) e.g. consistent typo mistake.
3. Interaction model is developed (aggregation of interaction pattern and linking with patient profile) e.g. visual problem and/or not good with keyboard/mouse.
4. Preferred interaction model is developed (how those model could be used to improve) Bigger fonts/High contrast mode and/or Touch based models/suggested keywords.
5. Translated interaction patterns (how new model will be used to change the way user completes the tasks/service) (e.g. Provide bigger fonts for instruction).
6. Capture new interaction events (to verify whether the modified pattern works and to re-calibrate above steps) (e.g. try and deploy each of the options one by one, until the interaction pattern improves)

Example 2

1. Interaction events capture (raw data) e.g Invalid option selection.
2. Interaction patterns (classification of way patient is interacting for specific tasks/service) e.g. consistent invalid choices.
3. Interaction model (aggregation of interaction pattern and linking with patient profile) e.g. Cognitive problem for instructions.
4. Preferred interaction model (how those model could be used to improve) Workflow/visual flow/Provide "May I help button".
5. Translated interaction patterns (how new model will be used to change the way user completes the tasks/service) (e.g. Provide simplified instruction or animated guidance).
6. Capture events (to verify whether the modified pattern works and to re-calibrate above steps) (e.g. try and deploy each of the options one by one, until the interaction pattern improves).

In another exemplary embodiment, a computer program or computer program element is provided that is characterized by being configured to execute the method steps of the method according to one of the preceding embodiments, an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

TABLE 1

| InteractionType | Interaction Description | Fields |
| --- | --- | --- |
| Login Session Summary | This interaction type summarizes the login session details. This is indicative of the number of times the user has interacted with the application | Total login attempts, Number of failed attempts, Number of revocations, Number of successful logins |
| Login Session Details | This interaction type captures details of each session like duration of each interaction, number of screens accessed, number of application errors. | Session Start Time, Session End Time, Session Duration, Number of login attempts, Number of activities accessed, Number of app errors, Number of system events, Session termination trigger (lockout/shutdown) |
| Measurement Entry Summaries | This interaction type captures information regarding the amount of time, number of erroneous entries by the user and other detailed information related to user entry of measurements in the application. | Activity Start Time, Activity End Time, Launcher Activity, Task Id, Measurement Type, Number of Entries, Displayed Units, Entry1__Deletes, Entry2__Deletes, Entry3__Deletes, Number of invalid submissions, Status (submitted/cancelled), Number of brightness level change events, Number of connectivity change events, Average battery__level for activity duration, Number of error events logged |

TABLE 1-continued

| InteractionType | Interaction Description | Fields |
|---|---|---|
| Measurement Task completion statistics | This interaction type captures the statistics related to measurement tasks assigned to the user as well as how the user has responded to the tasks. | Measurement Type, Number of task assignments, Number of on-time completions, |Average start time differential (Average(Time of first attempt at task − scheduled start time)), |Average end time differential (Average(task due datetime − time of completion)), Number of error events logged |
| Measurement Task summaries | This interaction type summarizes the information related to measurement task summaries | Task Id, Measurement Type, Scheduled Start time, First attempt at task, Due Datetime, Completion Datetime, Status, Intervention triggered, High Priority Flag set, Medium Priority Flag set, Low Priority Flag Set |
| Survey Entry Summaries | This interaction types summarizes the patient interaction while responding to surveys presented in the eCP application. In depth details like the time spent on each screen/each question in the survey is captured. | Activity Start Time, Activity End Time, Launcher Activity, Task Id, SurveyId, Total number of questions visited, Status (submitted/suspended), Survey start type (fresh/resumed), Average choice changes per question, Number of previous question traversals, Average time in a question, Number of brightness_level change events, Number of connectivity_change events, Average battery_level for activity duration |
| Survey Statistics | This interaction type captures statistics of how the patient interacts on the survey tasks presented by the eCP application | Survey Id, Number of task assignments, Number of suspensions, Number of successful completions, Average choice changes per question, Average previous question traversals, Question with maximum eyeball time, Average number of questions visited |

The invention claimed is:

1. A device configured to improve a user interaction with a user interface application, the device comprising:
at least one user interface configured to provide data for a user, wherein the data comprises first interaction data of the user with a plurality of user interaction fields of a first version of the user interface application;
a processor configured to:
cluster the interaction data into a plurality of groups,
apply first machine learning to the first interaction data to generate a decision tree model and to determine a contribution a specific user interaction field of the plurality of user interaction fields makes to a specific group of the plurality of groups,
modify the specific user interaction field to be specific to a patient condition on the basis of the determined contribution the specific user interaction field makes, and
cause a display configured to display a second version of the user interface application comprising the modified specific user interaction field;
the at least one user interface is further configured to capture second interaction data of the user with the second version of the user interface application;
apply second machine learning to the second interaction data of the second version of the user interface application to determine the contribution the modified specific user interaction field of the plurality of interaction fields makes to the specific group of the plurality of groups.

2. The device according to claim 1, wherein the at least one user interface is further configured to capture the first interaction data of the user with the plurality of interaction fields of the first version of the user interface application.

3. The device according to claim 1, wherein the at least one user interface is further configured to receive the first interaction data of the user with the plurality of interaction fields of the first version of the user interface application from a source external to the device.

4. The device according to claim 1, wherein the decision tree model is generated on the basis of the plurality of groups, and the processor is further configured to use the decision tree model to analyze the first interaction data.

5. The device according to claim 1, wherein the data for the user comprises the second interaction data of the user with the second version of the user interface application, the processor is further configured to modify the specific user interaction field on the basis of the determined contribution the modified specific user interaction field makes, and
the display is further configured to display a third version of the user interface application comprising the further modified specific user interaction field.

6. A system for use in improving a user interaction with a user interface application, comprising:
at least one user interface comprising a display, wherein the at least one user interface is configured to provide data for a user, the data comprising first interaction data of the user with a plurality of interaction fields of a first version of the user interface application;
a processor configured to:
cluster the interaction data into a plurality of groups,
apply first machine learning to the first interaction data to generate a decision tree model and to determine a contribution a specific user interaction field of the plurality of interaction fields makes to a specific group of the plurality of groups,
modify the specific user interaction field to be specific to a patient condition on the basis of the determined contribution the specific user interaction field makes, and
the display is configured to display a second version of the user interface application comprising the modified specific user interaction field;
the at least one user interface is further configured to capture second interaction data of the user with the second version of the user interface application;
apply second machine learning to the second interaction data of the second version of the user interface application to determine the contribution the modified specific user interaction field of the plurality of interaction fields makes to the specific group of the plurality of groups.

7. The system according to claim 6, wherein the user interface is further configured to capture the first interaction data of the user with the plurality of interaction fields of the first version of the user interface application.

8. The system according to claim 6, wherein the at least one user interface further comprises:
a data storage device configured to provide the first interaction data of the user with the plurality of interaction fields of the first version of the user interface application.

9. The system according to claim 8, wherein the data storage device is further configured to provide data for the user that comprises health data and/or a user profile.

10. A method for use in improving a user interaction with a user interface application, comprising:
providing data for a user, the data comprising first interaction data of the user with a plurality of interaction fields of a first version of the user interface application;
clustering the first interaction data into a plurality of groups;
applying first machine learning to the first interaction data to generate a decision tree model and to determine a contribution a specific user interaction field of the plurality of interaction fields makes to a specific group of the plurality of groups;
modifying the specific user interaction field to be specific to a patient condition on the basis of the determined contribution the specific user interaction field makes;
displaying a second version of the user interface application comprising the modified specific user interaction field;
capturing second interaction data of the user with the second version of the user interface application;
applying second machine learning to the second interaction data to determine the contribution the modified specific user interaction field of the plurality of interaction fields makes to the specific group of the plurality of groups.

11. The method according to claim 10, wherein the decision tree model is generated on the basis of the plurality of groups.

12. The method according to claim 11, wherein classifying new interaction data into one of the plurality of groups is undertaken using the decision tree model.

13. The method according to claim 10, further comprising:
further modifying the specific user interaction field on the basis of the determined contribution the modified specific user interaction field makes; and
displaying a third version of the user interface application comprising the further modified specific user interaction field.

14. A non-transitory computer-readable medium comprising instructions which, when being executed by a processing unit, cause the processing unit to carry out or control a method for improving a user interaction with a user interface application, the non-transitory, computer-readable medium comprising:
instructions for providing data for a user, the data comprising first interaction data of the user with a plurality of interaction fields of a first version of the user interface application;
instructions for clustering the first interaction data into a plurality of groups;
instructions for applying first machine learning to the first interaction data to generate a decision tree model and to determine a contribution a specific user interaction field of the plurality of interaction fields makes to a specific group of the plurality of groups;
instructions for modifying the specific user interaction field to be specific to a patient condition on the basis of the determined contribution the specific user interaction field makes;
instructions for displaying a second version of the user interface application comprising the modified specific user interaction field;
instructions for capturing second interaction data of the user with the second version of the user interface application;
instructions for applying second machine learning to the second interaction data to determine the contribution the modified specific user interaction field of the plurality of interaction fields makes to the specific group of the plurality of groups.

* * * * *